US011521743B2

(12) United States Patent
Wang et al.

(10) Patent No.: US 11,521,743 B2
(45) Date of Patent: Dec. 6, 2022

(54) FRAMEWORK FOR PERFORMING ELECTROCARDIOGRAPHY ANALYSIS

(71) Applicant: TENCENT AMERICA LLC, Palo Alto, CA (US)

(72) Inventors: Xu Wang, Palo Alto, CA (US); Kun Wang, San Jose, CA (US); Shangqing Zhang, San Jose, CA (US); Min Tu, Cupertino, CA (US); Xiaozhong Chen, Cedarburg, WI (US); Wei Fan, New York, NY (US)

(73) Assignee: TENCENT AMERICA LLC, Palo Alto, CA (US)

( * ) Notice: Subject to any disclaimer, the term of this patent is extended or adjusted under 35 U.S.C. 154(b) by 207 days.

(21) Appl. No.: 16/658,943

(22) Filed: Oct. 21, 2019

(65) Prior Publication Data
US 2021/0118566 A1   Apr. 22, 2021

(51) Int. Cl.
*G16H 50/20* (2018.01)
*G06N 3/04* (2006.01)
*G16H 30/40* (2018.01)

(52) U.S. Cl.
CPC .......... *G16H 50/20* (2018.01); *G06N 3/0454* (2013.01); *G16H 30/40* (2018.01)

(58) Field of Classification Search
CPC ......... G16H 10/00–80/00; G06N 3/00–99/007
See application file for complete search history.

(56) References Cited

U.S. PATENT DOCUMENTS

2003/0216655 A1* 11/2003 Schreck ................. A61B 5/327
                                                              600/509
2006/0018525 A1*  1/2006 Barbour ............. A61B 5/02007
                                                              382/128
(Continued)

FOREIGN PATENT DOCUMENTS

CN          108175402 A   *  6/2018
CN          109620211 A   *  4/2019   ............. A61B 5/318
(Continued)

OTHER PUBLICATIONS

He et al., "Automatic Cardiac Arrhythmia Classification Using Combination of Deep Residual Network and Bidirectional LSTM," IEEE Access, vol. 7 (2019) pp. 102119-102135. (Year: 2019).*
(Continued)

*Primary Examiner* — Jonathon A. Szumny
(74) *Attorney, Agent, or Firm* — Sughrue Mion, PLLC

(57) ABSTRACT

A method and device for performing electrocardiography (ECG) analysis, the method including receiving ECG data that is from one or more leads, generating an image based on the ECG data, obtaining a feature map based on the image, inputting the feature map to a first neural network, the first neural network configured to generate an output based on the feature map inputted, inputting the output of the first neural network to a second neural network, the second neural network configured to obtain at least one temporal feature of the image based on the output of the first neural network and a previous state of the second neural network, and classifying a signal included in the ECG data based on the at least one temporal feature obtained by the second neural network.

18 Claims, 10 Drawing Sheets

(56) References Cited

U.S. PATENT DOCUMENTS

| | | | | |
|---|---|---|---|---|
| 2007/0208263 | A1* | 9/2007 | John | A61B 5/349 600/509 |
| 2016/0113586 | A1* | 4/2016 | Hemming | A61B 5/318 600/510 |
| 2017/0112401 | A1* | 4/2017 | Rapin | A61B 5/7264 |
| 2017/0156614 | A1 | 6/2017 | Ibanez Catala | |
| 2017/0265765 | A1* | 9/2017 | Baumann | A61B 5/339 |
| 2018/0374213 | A1 | 12/2018 | Arnold et al. | |
| 2019/0059763 | A1* | 2/2019 | Shakur | A61B 5/72 |
| 2019/0167143 | A1* | 6/2019 | Li | G16H 50/20 |
| 2020/0160980 | A1* | 5/2020 | Lyman | A61B 5/7264 |
| 2020/0178825 | A1* | 6/2020 | Lu | A61B 5/363 |

FOREIGN PATENT DOCUMENTS

| | | | |
|---|---|---|---|
| CN | 110236525 A * | 9/2019 | |
| CN | 110313894 A * | 10/2019 | |
| WO | WO-2010018500 A1 * | 2/2010 | A61B 6/463 |
| WO | WO-2018119316 A1 * | 6/2018 | A61B 5/0205 |
| WO | WO-2019024861 A1 * | 2/2019 | G06N 3/0454 |
| WO | 2019046854 A1 | 3/2019 | |
| WO | WO-2019212833 A1 * | 11/2019 | A61B 5/0004 |
| WO | WO-2020077198 A1 * | 4/2020 | |

OTHER PUBLICATIONS

Chen et al., "A cascaded classifier for multi-lead ECG based on feature fusion," Computer Methods and Programs in Biomedicine 178 (2019) pp. 135-143. (Year: 2019).*

Liu et al., "An Attention-based Hybrid LSTM-CNN Model for Arrhythmias Classification," International Joint Conference on Neural Networks, Budapest, Hungary Jul. 14-19, 2019, pp. 1-8. (Year: 2019).*

Wei et al., "Atrial Fibrillation Detection by the Combination of Recurrence Complex Network and Convolutional Neural Network," Journal of Probability and Statistics, vol. 2019, Article ID 8057820, pp. 1-9. (Year: 2019).*

Cao et al., "Atrial Fibrillation Detection Using an Improved Multi-Scale Decomposition Enhanced Residual Convolutional Neural Network," IEEE Access, vol. 7 (2019) pp. 89152-89161. (Year: 2019).*

Nassim Ammour, "Atrial Fibrillation Detection with a Domain Adaptation Neural Network Approach," 2018 International Conference on Computational Science and Computational Intelligence (CSCI), pp. 738-743 (Year: 2018).*

Schwab et al., "Beat by Beat: Classifying Cardiac Arrhythmias with Recurrent Neural Networks," Computing in Cardiology 2017, vol. 44, pp. 1-4. (Year: 2017).*

Shenda Hong et al., "Combining deep neural networks and engineered features for cardiac arrhythmia detection from ECG recordings," 2019 Physiol. Meas. 40 054009, pp. 1-12. (Year: 2019).*

Xia et al., "Detecting atrial fibrillation by deep convolutional neural networks," Computers in Biology and Medicine 93 (2018) 84-92. (Year: 2018).*

Shashikumar et al., "Detection of Paroxysmal Atrial Fibrillation using Attention-based Bidirectional Recurrent Neural Networks," Applied Data Science Track Paper KDD 2018, Aug. 19-23, 2018, London, United Kingdom, pp. 715-723. (Year: 2018).*

Li et al, "Dual-Input Neural Network Integrating Feature Extraction and Deep Learning for Coronary Artery Disease Detection Using Electrocardiogram and Phonocardiogram," IEEE Access, vol. 7 (2019) pp. 146457-146469. (Year: 2019).*

Homaeinezhad et al., "ECG arrhythmia recognition via a neuro-SVM-KNN hybrid classifier with virtual QRS image-based geometrical features," Expert Systems with Applications 39 (2012) 2047-2058. (Year: 2012).*

Guler et al., "ECG beat classifier designed by combined neural network model," Pattern Recognition 38 (2005) 199-208. (Year: 2005).*

Addison et al., "Evaluating Arrhythmias in ECG Signals Using Wavelet Transforms," IEEE Engineering in Medicine and Biology, Sep./Oct. 2000, pp. 104-109. (Year: 2000).*

"ResNet (34, 50, 101): Residual CNNs for Image Classification Tasks," https://neurohive.io/en/popular-networks/resnet/, Jan. 23, 2019. (Year: 2019).*

Written Opinion in International Application No. PCT/US2020/47136, dated Nov. 20, 2020.

International Search Report in International Application No. PCT/US2020/47136, dated Nov. 20, 2020.

* cited by examiner

FRAMEWORK FOR PERFORMING ELECTROCARDIOGRAPHY ANALYSIS

BACKGROUND

An electrocardiogram records the electrical signals in a heart. It is a common test to detect heart problems such as atrial fibrillation (AFib), ventricular fibrillation (VFib), and myocardial infarction. Most conventional approaches for electrocardiography (ECG) analysis are based on one-dimensional digital signals. These methods apply digital signal processing algorithms such as wavelet transformation to extract features from ECG signals such as P wave and R wave intervals. However, these approaches lack reliability when some features are missed from detection. Some approaches apply a neural network for AFib detection. These networks are very shallow and not able to capture contextual features.

SUMMARY

According to embodiments, a method of performing electrocardiography (ECG) analysis by at least one processor includes receiving ECG data that is from one or more leads; generating an image based on the ECG data; obtaining a feature map, based on the image; inputting the feature map to a first neural network, the first neural network configured to generate an output based on the feature map inputted; inputting the output of the first neural network to a second neural network, the second neural network configured to obtain at least one temporal feature of the image based on the output of the first neural network and a previous state of the second neural network; and classifying a signal included in the ECG data based on the at least one temporal feature obtained by the second neural network.

According to embodiments, a device for performing electrocardiography (ECG) analysis comprises at least one memory configured to store computer program code, and at least one processor configured to access said computer program code and operate as instructed by said computer program code. The computer program code includes image generation code configured to cause the at least one processor to generate an image based on ECG data received by the device from one or more leads. The computer program code furthing including feature extraction code configured to cause the at least one processor to obtain a feature map, based on the image, input the feature map to a first neural network, the first neural network configured to generate an output based on the feature map inputted, input the output of the first neural network to a second neural network, the second neural network configured to obtain at least one temporal feature of the image based on the output of the first neural network and a previous state of the second neural network. The computer program code further inlcuding classification code configured to cause the at least one processor to classify a signal included in the ECG data based on the at least one temporal feature obtained by the second neural network.

According to embodiments, a non-transitory computer-readable medium stores instructions comprising one or more instructions that, when executed by at least one processor for performing electrocardiography (ECG) analysis, cause the at least one processor to receive ECG data that is from one or more leads; generate an image based on the ECG data; obtain a feature map, based on the image; input the feature map to a first neural network, the first neural network configured to generate an output based on the feature map inputted; input the output of the first neural network to a second neural network, the second neural network configured to obtain at least one temporal feature of the image based on the output of the first neural network and a previous state of the second neural network; and classify a signal included in the ECG data based on the at least one temporal feature obtained by the second neural network.

BRIEF DESCRIPTION OF THE DRAWINGS

Further features, the nature, and various advantages of the disclosed subject matter will be more apparent from the following detailed description and the accompanying drawings in which.

DETAILED DESCRIPTION

Atrial fibrillation (AFib) and ventricular fibrillation (VFib) are two kinds of arrhythmia encountered in clinical practice. Most detection methods of AFib and VFib involves electrocardiography (ECG) analysis. An ECG test records the electrical activity of a heart and displays the impulses as waves. An injured heart will conduct irregular impulses, which leads to flutter waves in the ECG.

In at least one embodiment of the present disclosure, a deep teaming based system and method is provided to detect the irregular impulses and classify between regular heartbeats and AFib or VFib. For example, a system of an embodiment of the present disclosures takes ECG signals, that are one-dimensional signals, as an input, transforms the one-dimensional ECG signals into multi-dimensional image sequences, which encodes more temporal and spatial information. Then, the data is fed into a deep learning based model training framework of the system for AFib and VFib detection. In an embodiment of the present disclosure, the deep learning based model training framework may be achieved with techniques that use, for example, an image generation module, a feature extraction module, and a signal classification module that, in combination, perform the functions of a data processing module and a detection module.

Some embodiments of the present disclosure may read ECG signals and automatically detect AFib or VFib. Some embodiments of the present disclosure are not restricted to single-lead or multiple-lead signals. Some embodiments of the present disclosure may convert traditional one-dimensional ECG signals to two-dimensional images, which provides a more reliable and efficient way to train a model. Some embodiments of the present disclosure achieve better performance and can be applied in multiple areas of ECG analysis, especially for computer-assisted diagnosis.

An embodiment of the present disclosure provides a robust and efficient way to detect AFib and VFib. For example, an at least one processor performing the framework may convert normal and AFib or VFib ECG signals from different leads into sequences of images. The at least one processor performing the framework may extract deep features by training a deep neural network model(s), which is more reliable than hand-crafted features when dealing with complicated input signals. The at least one processor performing the framework is able to distinguish between normal heart beat and AFib or VFib regardless of which lead the data comes from. Accordingly, embodiments of the present disclosure save lots of time and manual work to analyze ECG signals, and can be applied in many ECG analysis tasks, such as computer-aided diagnosis and ECG monitoring.

Figure 1:
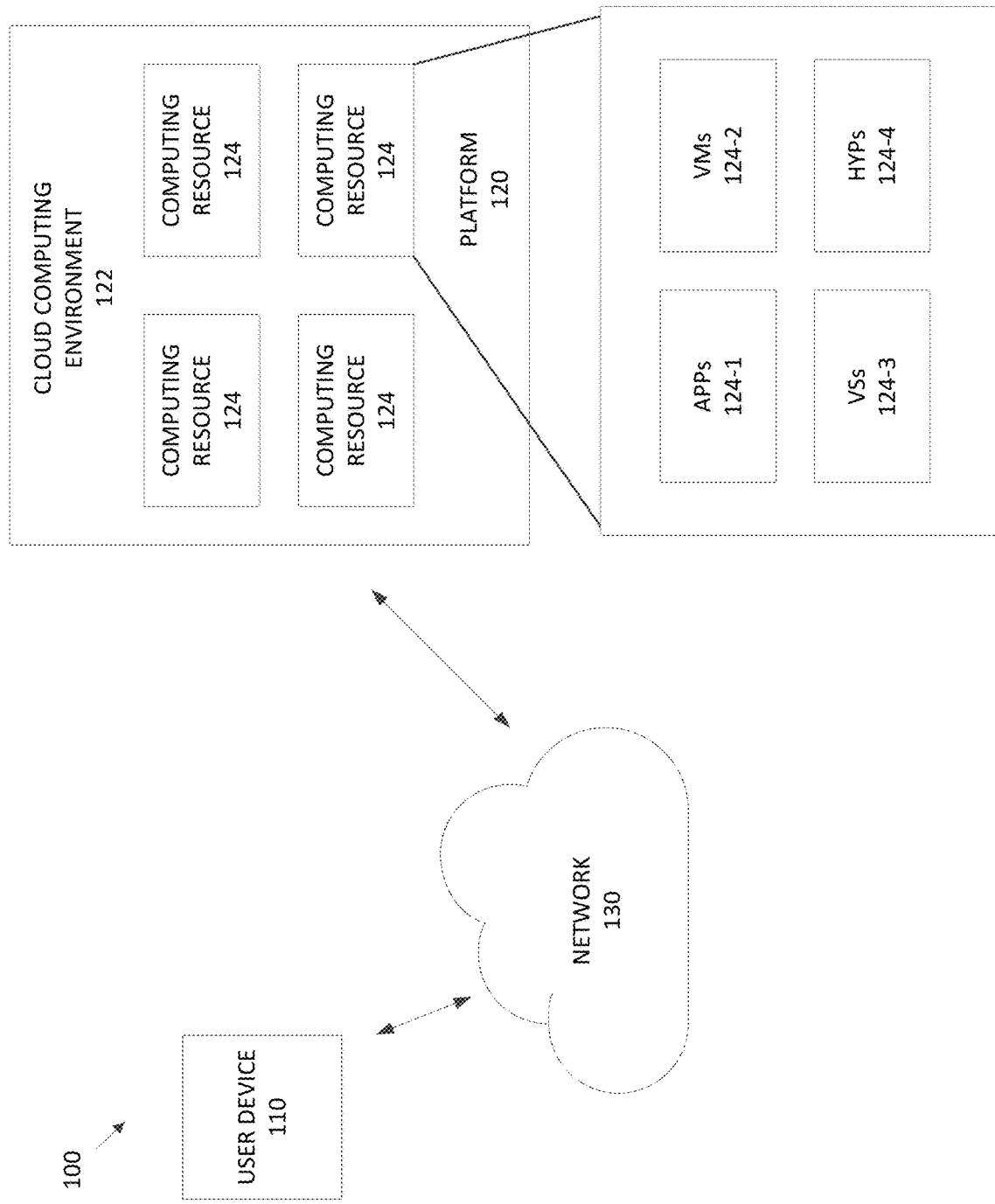
FIG. 1 is a diagram of an environment in which methods, apparatuses, and systems described herein may be implemented, according to embodiments.

FIG. 1 is a diagram of an environment 100 in which methods, apparatuses and systems described herein may be implemented, according to embodiments. As shown in FIG. 1, environment 100 may include a user device 110, a platform 120, and a network 130. Devices of environment 100 may interconnect via wired connections, wireless connections, or a combination of wired and wireless connections.

User device 110 includes one or more devices capable of receiving, generating, storing, processing, anchor providing information associated with platform 120. For example, user device 110 may include a computing device (e.g., a desktop computer, a laptop computer, a tablet computer, a handheld computer, a smart speaker, a server, etc.), a mobile phone (e.g., a smart phone, a radiotelephone, etc.), a wearable device (e.g., a pair of smart glasses or a smart watch), or a similar device. In some implementations, user device 110 may receive information from and/or transmit information to platform 120.

Platform 120 includes one or more devices as described elsewhere herein. In some implementations, platform 120 may include a cloud server or a group of cloud servers. In some implementations, platform 120 may be designed to be modular such that software components may be swapped in or out depending on a particular need. As such, platform 120 may be easily and/or quickly reconfigured for different uses.

In some implementations, as shown, platform 120 may be hosted in cloud computing environment 122. Notably, while implementations described herein describe platform 120 as being hosted in cloud computing environment 122, in some implementations, platform 120 is may not be cloud-based (i.e., may be implemented outside of a cloud computing environment) or may be partially cloud-based.

Cloud computing environment 122 includes an environment that hosts platform 120. Cloud computing environment 122 may provide computation, software, data access, storage, etc. services that do not require end-user (e.g., user device 110) knowledge of a physical location and configuration of system(s) and/or device(s) that hosts platform 120. As shown, cloud computing environment 122 may include a group of computing resources 124 (referred to collectively as "computing resources 124" and individually as "computing resource 124").

Computing resource 124 includes one or more personal computers, workstation computers, server devices, or other types of computation and/or communication devices. In some implementations, computing resource 124 may host platform 120. The cloud resources may include compute instances executing in computing resource 124, storage devices provided in computing resource 124, data transfer devices provided by computing resource 124, etc. In some implementations, computing resource 124 may communicate with other computing resources 124 via wired connections, wireless connections, or a combination of wired and wireless connections.

As further shown in FIG. 1, computing resource 4 includes a group of cloud resources, such as one or more applications (APPs) 124-1, one or more virtual machines (VMs) 124-2, virtualized storage (VSs) 124-3, one or more hypervisors (HYPs) 124-4, or the like.

Application 124-1 includes one or more software applications that may be provided to or accessed by user device 110 and/or platform 120. Application 124-1 may eliminate a need to install and execute the software applications on user device 110. For example, application 124-1 may include software associated with platform 120 and/or any other software capable of being provided via cloud computing environment 122. In some implementations, one application 124-1 may send/receive information to/from one or more other applications 124-1, via virtual machine 124-2.

Virtual machine 124-2 includes a software implementation of a machine (e.g., a computer) that executes programs like a physical machine. Virtual machine 124-2 may be either a system virtual machine or a process virtual machine, depending upon use and degree of correspondence to any real machine by virtual machine 124-2. A system virtual machine may provide a complete system platform that supports execution of a complete operating system (OS). A process virtual machine may execute a single program, and may support a single process. In so implementations, virtual machine 124-2 may execute on behalf of a user (e.g., user device 110), and may manage infrastructure of cloud computing environment 122, such as data management, synchronization, or long-duration data transfers.

Virtualized storage 124-3 includes one or more storage systems and/or one or more devices that use virtualization techniques within the storage systems or devices of computing resource 124. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 124-4 may provide hardware virtualization techniques that allow multiple operating systems (e.g., "guest operating systems") to execute concurrently on a host computer, such as computing resource 124. Hypervisor 124-4 may present a virtual operating platform to the guest operating systems, and may manage the execution of the guest operating systems. Multiple instances of a variety of operating systems may share virtualized hardware resources.

Network 130 includes one or more wired and/or wireless networks. For example, network 130 may include a cellular network (e.g., a fifth generation (5G) network, a long-term evolution (LTE) network, a third generation (3G) network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, or the like, and/or a combination of these or other types of networks.

The number and arrangement of devices and networks shown in FIG. 1 are provided as an example. In practice, there may be additional devices and/or networks, fewer devices and/or networks, different devices and/or networks, or differently arranged devices and/or networks than those shown in FIG. 1. Furthermore, two or more devices shown in FIG. 1 may be implemented within a single device, or a single device shown in FIG. 1 may be implemented as multiple, distributed devices. Additionally, or alternatively, a set of devices (e.g., one or more devices) of environment 100 may perform one or more functions described as being performed by another set of devices of environment 100.

Figure 2:
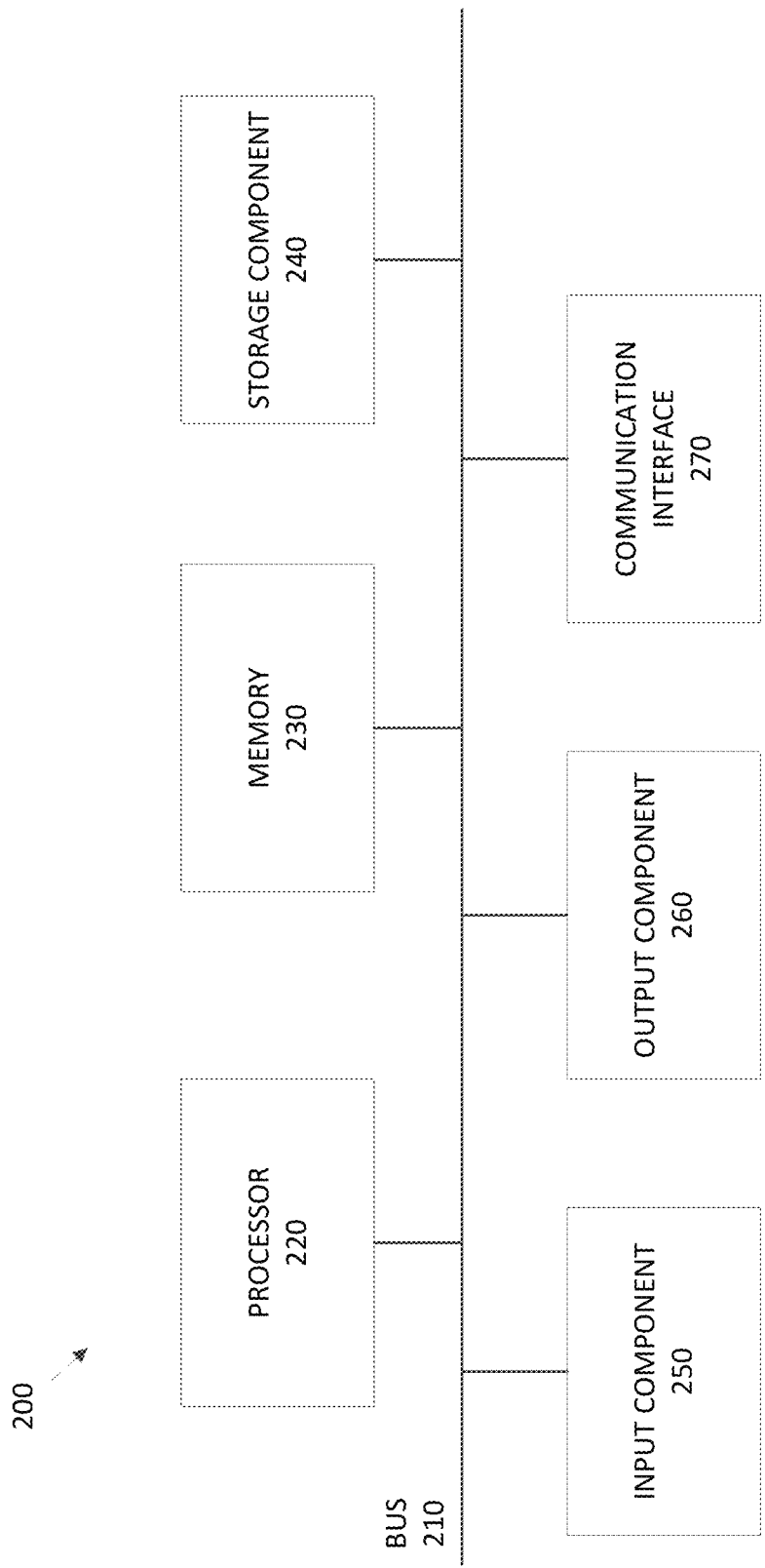
FIG. 2 is a diagram of example components of one or more devices of FIG. 1.

FIG. 2 is a diagram of example components of one or more devices of FIG. 1. A device 200 may correspond to user device 110 and/or platform 120. As shown in FIG. 2, device 200 may include a bus 210, a processor 220, a memory 230, a storage component 240, an input component 250, an output component 260, and a communication interface 270.

Bus 210 includes a component that permits communication among the components of device 200. Processor 220 is implemented in hardware, firmware, or a combination of hardware and software. Processor 220 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 220 includes one or more processors capable of being programmed to perform a function. Memory 230 includes a random access memory (RAM), a read only memory (ROM), and/or another type of dynamic or static storage device (e.g., a flash memory, a magnetic memory, and/or an optical memory) that stores information and/or instructions for use by processor 220.

Storage component 240 stores information and/or software related to the operation and use of device 200. For example, storage component 240 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 250 includes a component that permits device 200 to receive information, such as via user input (e.g., a touch screen display, a keyboard, a keypad, a mouse, a button, a switch, and/or a microphone). Additionally, or alternatively, input component 250 may include a sensor for sensing information (e.g., a global positioning system (GPS) component, an accelerometer, a gyroscope, and/or an actuator). Output component 260 includes a component that provides output information from device 200 (e.g., a display, a speaker, and/or one or more light-emitting diodes (LEDs)).

Communication interface 270 includes a transceiver-like component (e.g., a transceiver and/or a separate receiver and transmitter) that enables device 200 to communicate with other devices, such as via a wired connection, a wireless connection, or a combination of wired and wireless connections. Communication interface 270 may permit device 200 to receive information from another device and/or provide information to another device. For example, communication interface 270 may include an Ethernet interface, an optical interface, a coaxial interface, an infrared interface, a radio frequency (RF) interface, a universal serial bus (USB) interface, a Wi-Fi interface, a cellular network interface, or the like.

Device 200 may perform one or more processes described herein. Device 200 may perform these processes in response to processor 220 executing software instructions stored by a non-transitory computer-readable medium, such as memory 230 and/or storage component 240. A computer-readable medium is defined herein as a non-transitory memory device. A memory device includes memory space within a single physical storage device or memory space spread across multiple physical storage devices.

Software instructions may be read into memory 230 and/or storage component 240 from another computer-readable medium or from another device via communication interface 270. When executed, software instructions stored in memory 230 and/or storage component 240 may cause processor 220 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 2 are provided as an example. In practice, device 200 may include additional components, fewer components, different components, or differently arranged components than those shown in FIG. 2. Additionally, or alternatively, a set of components (e.g., one or more components) of device 200 may perform one or more functions described as being performed by another set of components of device 200.

Figure 3:
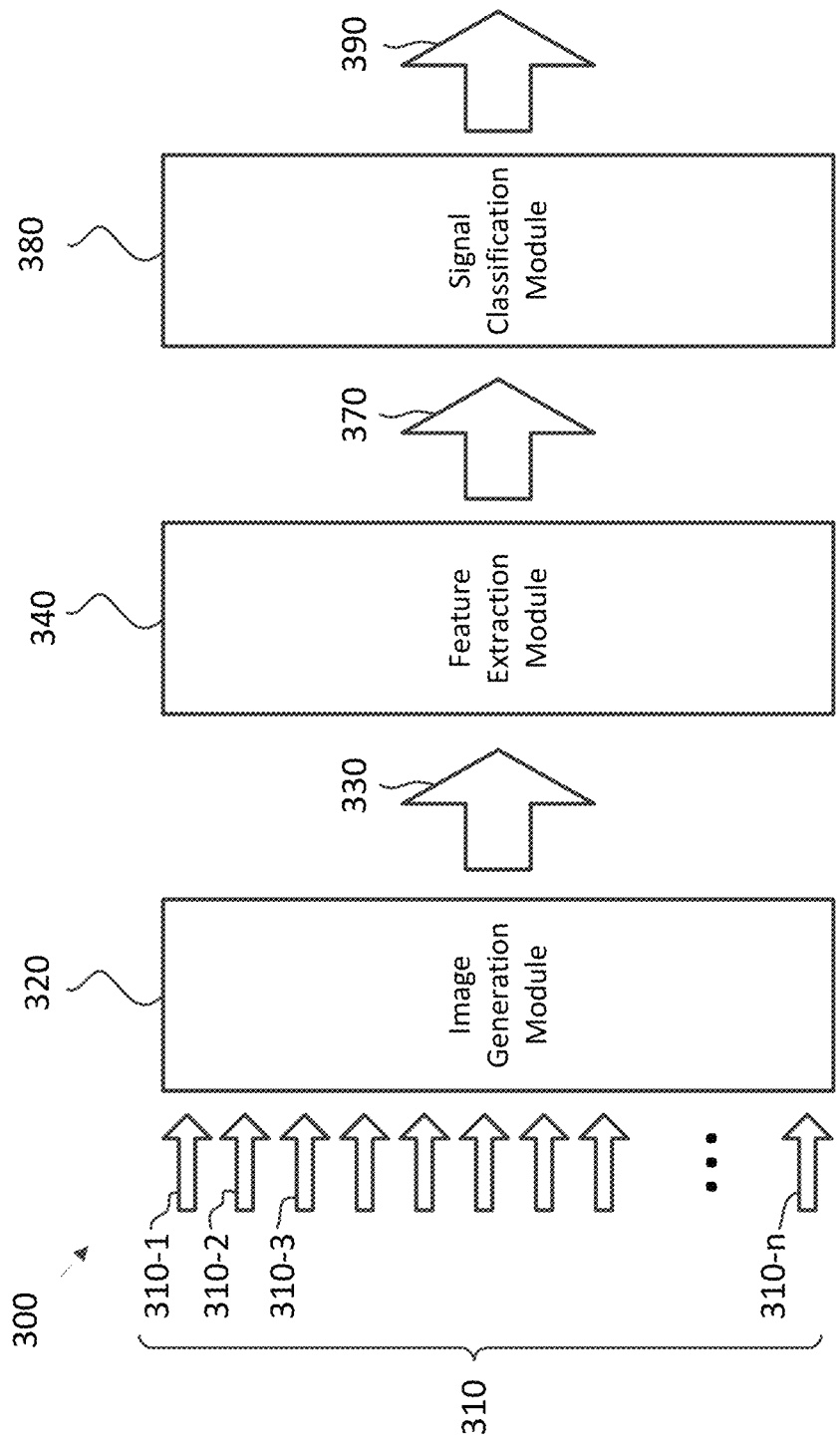
FIG. 3 is a diagram of an architecture for an MG-ECG analysis framework of an embodiment.

As illustrated in FIG. 3, an embodiment of the present disclosure may include a framework 300 comprising an image generation module 320, a feature extraction module 340, and a signal classification module 380.

Figure 4:
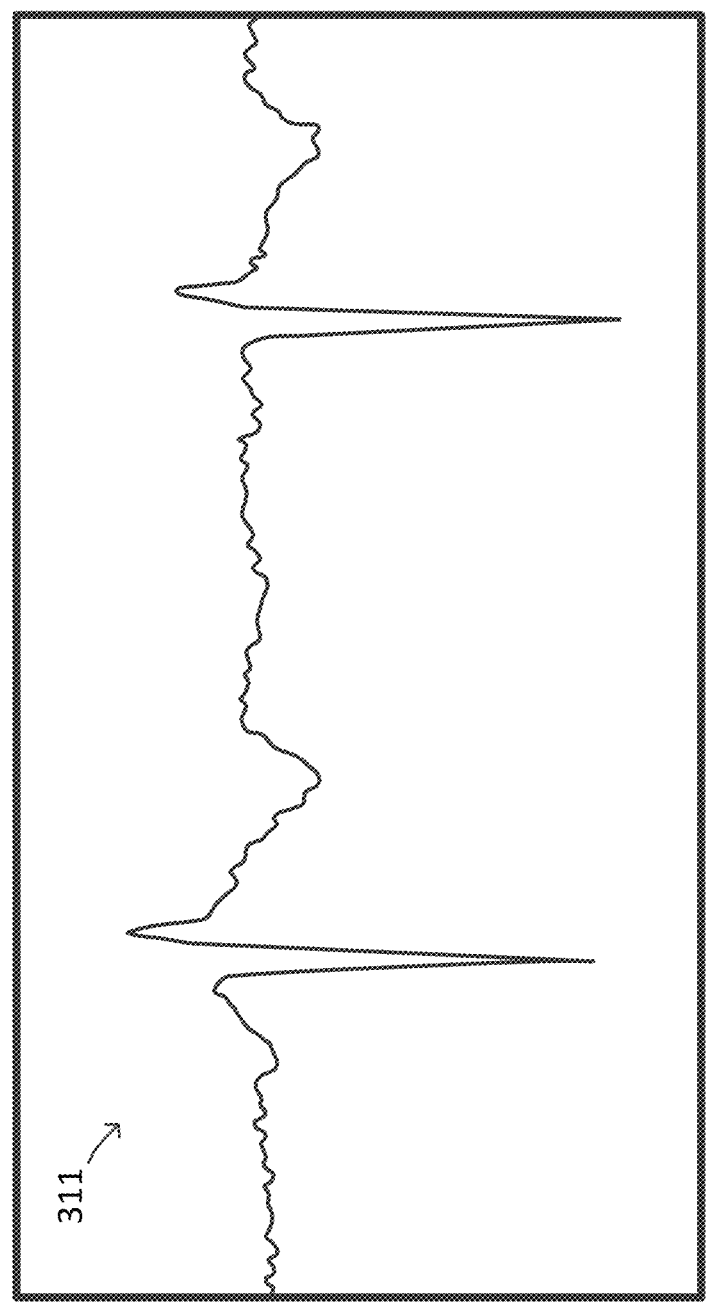
FIG. 4 illustrates an example of an ECG signal.

The image generation module 320 may take ECG signals 310 as an input, including signals 310-1, 310-2, 310-3, and up to ECG signal 310-n. The ECG signals 310 may each be a traditional one-dimensional (1D) ECG signal as, for example, represented by the signal 311 illustrated in FIG. 4. The ECG signals 310 may be taken from standard ECG data, which contains signals from different leads that require multiple electrodes in contact a body. For example, the standard ECG data may include different leads that requires 10 electrodes in contact with the body. In an embodiment, the ECG signals 310 received by the image generation module 320 may be single-lead or multi-lead signals.

The image generation module 320 may convert the one-dimensional ECG signals 310 received to image sequences 330 that are output to the feature extraction module 340.

Figure 5:
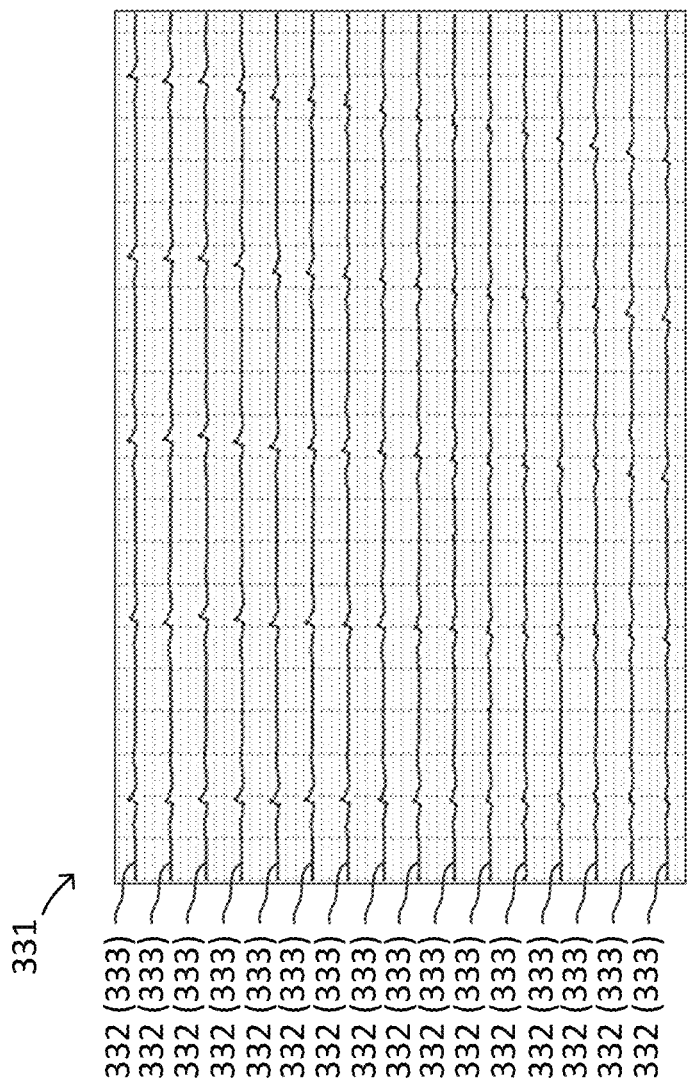
FIG. 5 illustrates an example of a three-dimensional plot generated by an embodiment.

For example, with reference to FIG. 5, the image generation module 320 can generate one or more three dimensional plots 331, wherein each three dimension plot 331 includes a plurality of generated two dimensional (2D) plots 332, and each 2D plot 332 represents a respective 1D signal 333. In an embodiment, each 2D plot 332 may have a height dimension and a width dimension, and the three dimension plot 331 may include a height dimension, a width dimension, and a channel dimension. In an embodiment, the width dimension may correspond to time, the height dimension may correspond to intensity, and each channel of the channel dimension may correspond to a respective one of the 2D plots 332.

In an embodiment, the image generation module 320 can generate one or more of the three dimensional plots 331, wherein each three dimensional plot 331 includes information of one or more leads. For example, the image generation module 320 may generate a respective 2D plot 332 for each of the leads that are associated with a respective one of the ECG signals 310 and stack them together into a single 3D plot 331. In an embodiment, each of the 1D signals 332 represented by a respective 2D plot 332 may be at least a portion of a respective one of the ECG signals 310 of a corresponding lead. Each 1D signal 333 may include one or more peaks from a respective one of the ECG signals 310 from a respective lead. As an example, referring to FIG. 5, each 1D signal 333 may have 5 peaks. The image generation module 320 may generate each 1D signal 333 by detecting peaks of a respective one of the ECG signals 310, extracting signal portions, from different time frames, of the respective one of the ECG signals 310 based on the peaks detected, and stacking the signal portions. For example, for a 1D signal 333 including at least a portion of ECG signal 310-1, the image generation module 320 may extract a first 1D signal starting at a first peak position of the ECG signal 310-1, a second 1D signal starting at a second peak position of the ECG signal 310-1, and so on, and then stacking the 1D signals together to form a 1D signal 333 of the 2D plot 332.

In an embodiment, the image generation module 320 can generate a plurality of the three dimensional plots 331, wherein a respective three dimensional plot 331 is generated for each lead. For example, each three dimensional plot 331 may include information of only a respective one of the ECG signals 310. Each 2D plot 332 of a three dimensional plot 331 may correspond to a respective time frame of a same ECG signal 310 of a same lead, and include one or more peaks from the same ECG signal 310. For example, with reference to FIG. 5, each of the 1D signals 332 represented by a respective 2D plot 332 may be a respective portion of a same ECG signal 310 of a same lead. Each 1D signal 333 may include one or more respective peaks from the same ECG signal 310 from the same lead. As an example, referring to FIG. 5, each 1D signal 333 may have 5 peaks. The image generation module 320 may generate each 1D signal 333 by detecting peaks of the same ECG signal 310, extracting signal portions, from different time frames, of the same ECG signal 310 based on the peaks detected, and stacking the 1D signals 333 to form the 3D plot 331. For example, for a 3D plot 331 corresponding to ECG signal 310-1, the image generation module 320 may extract a first 1D signal starting at a first peak position of the ECG signal 310-1 to form a first one of the 2D plots 332, extract a second 1D signal starting at a second peak position of the ECG signal 310-1 to form a second one of the 2D plots 332, and so on, and then stacking the 2D plots 332 together to form a 3D plot 331.

Figure 6:
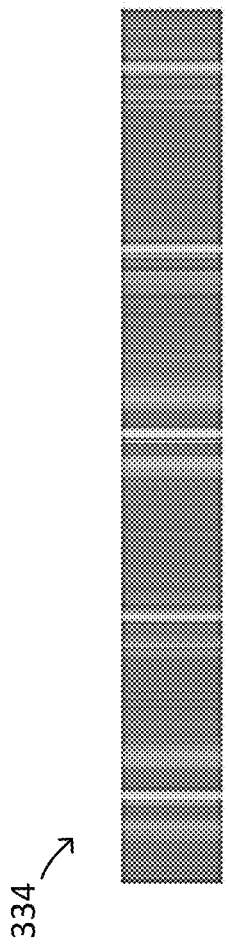
FIG. 6 illustrates an example of a waterfall plot generated by an embodiment.

In an embodiment, the image generation module 320 can generate the 3D plots 331 as one or more of the image sequences 330. In an embodiment, with reference to FIG. 6, the image generation module 320 can generate a respective waterfall plot 334 for one or more of the 3D plots 331, and use the waterfall plots 334 as one or more of the image sequences 330. The image generation module 320 may generate a waterfall plot 334 by stacking a plurality of the 2D plots 332. In an embodiment, the image generation module 320 may generate one or more 3D waterfall plot 333 so as to each include information for a plurality of leads, or generate a respective waterfall plot 334 for each of the leads.

The image generation module 320 may, for example, record a fixed length of the ECG signals 310 from a heartbeat, and stack a sequence of the ECG signals 310 to generate the waterfall plot 334. The waterfall plot 334 of normal heartbeats is clean and consistent while, for AFib or VFib, the waterfall plot 334 is noisy and inconsistent. After creating the image sequence 330, the framework 300 can extract features from the image sequence 330 and classify between normal and AFib or VFib image sequences.

In the embodiment, the framework 300 may take each lead as a single input. The framework may train a classification network from ECG signals 310 received from the leads. Accordingly, the framework 300 may classify the ECG signals no matter which lead the ECGs signals 310 come from.

Figure 7:
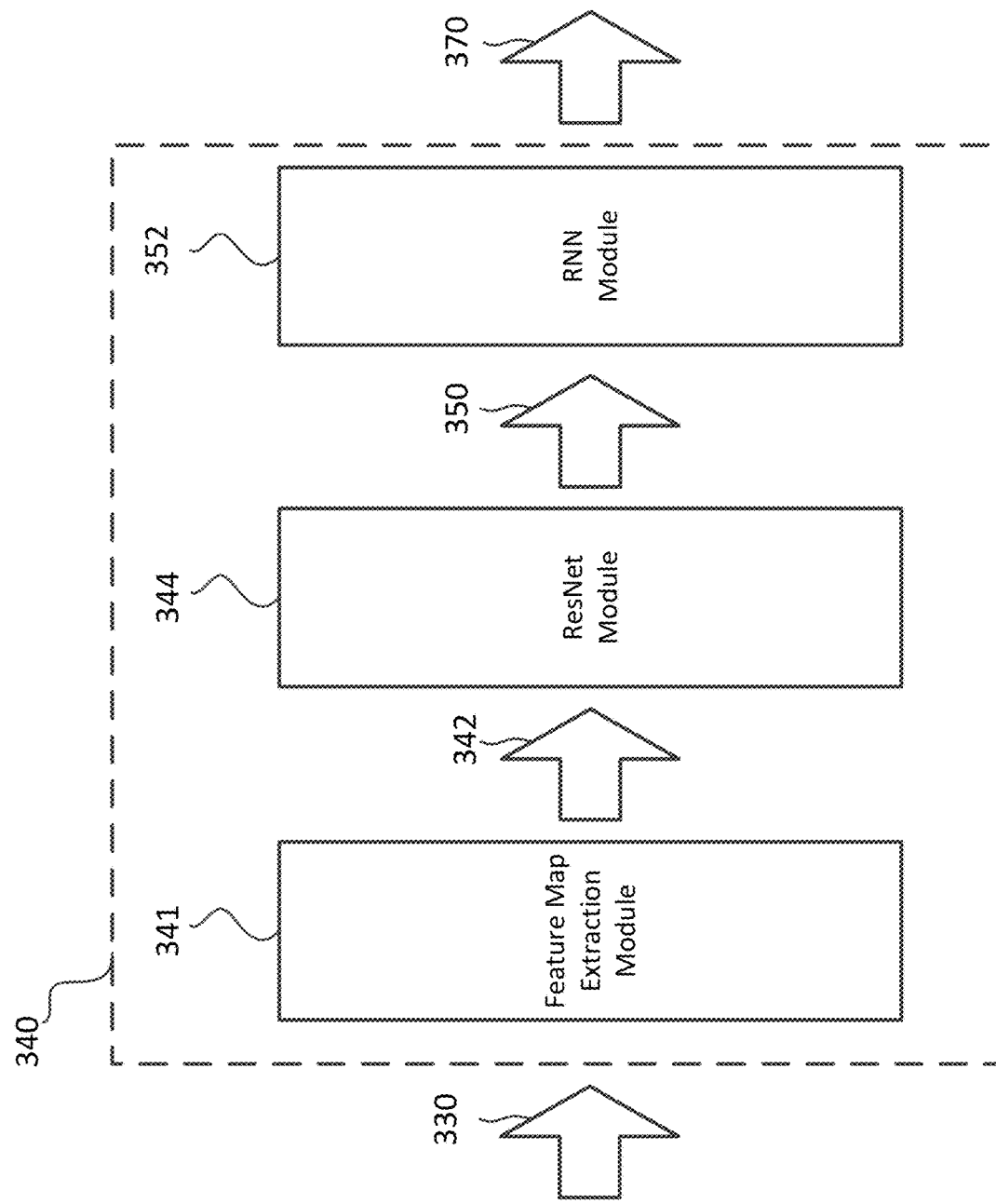
FIG. 7 is a diagram illustrating a feature extraction module of an embodiment.

For example, the image generation module 320 may output the image sequence(s) 330 to the feature extraction module 340. As shown in FIG. 7, the feature extraction module 340 may include, for example, a feature map extraction module 341, a residual neural network (ResNet) module 344, and a recurrent neural network (RNN) module 352.

The feature map extraction module 341 may be, for example, a convolution network that extracts a feature map 342 from a waterfall image of the image sequence 330, and sends the feature map 342 to the ResNet module 344.

Figure 9:
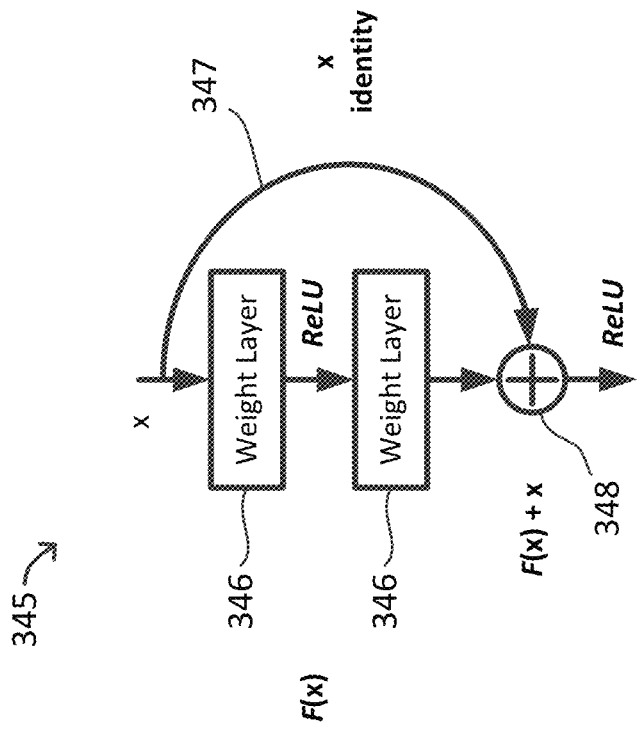
FIG. 9 is a diagram illustrating a ResNet block of a ResNet module of an embodiment.
Figure 8:
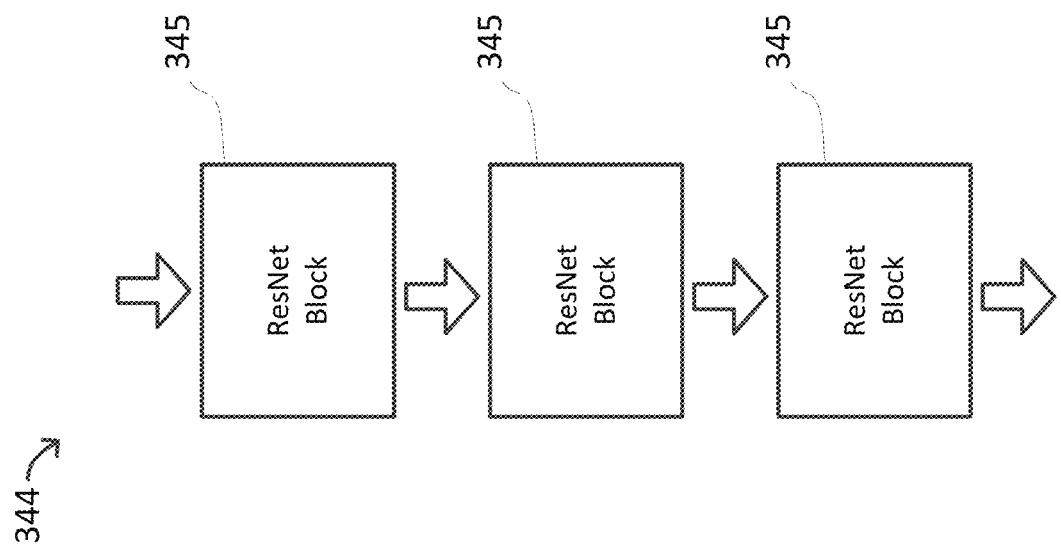
FIG. 8 is a diagram illustrating a ResNet module of a feature extraction module of an embodiment.

The ResNet module 344 may receive the feature map 342 and output features 350 to the RNN module 352. The ResNet module 344 may be trained. As illustrated in FIG. 8, the ResNet module 344 may include a plurality of ResNet blocks 345. While FIG. 8 illustrates three ResNet blocks 345, the ResNet module 344 may include any number of ResNet blocks 345. With reference to FIG. 9, each ResNet block 345 may include a convolutional network. For example, each Resnet block 345 may include one or more weight layers 346, wherein at least one of the weight layers 346 is associated with a rectified linear unit (ReLU).

With respect to a first ResNet block 345 (e.g. the top ResNet Block 345 illustrated in FIG. 8), the ResNet block 345 may receive the feature map 342 as an input (corresponding to "x"), input the feature map 342 into the weight layers 346 to generate an output (corresponding to "F(x)") that is a convolution feature, and save the feature map 342 as a shortcut 347 (corresponding to "x identity"). An addition layer 348 of the ResNet block 345 may then add together the convolution feature, outputted from the weight layers 346, and the shortcut 347, wherein the addition layer 348 may be associated with a ReLU layer. The output of the addition layer 348 may be input to an adjacent one of the ResNet blocks 345 as the input ("x") of such ResNet block 345, and the output of such ResNet block 345 may be the input of the following Resnet block 345, and so on to repeat the process with each of the Resnet Blocks 345 in the ResNet module 344, to generate an output 350 of at least one feature that is sent to the RNN module 352, wherein features from the ResNet Module 344 are fed to the RNN module 352 to extract temporal features 370 from the ECG signals 310 and output the temporal features 370, wherein the temporal features 370 are, for example, features between heartbeats. The RNN module 352 may be trained.

Figure 10:
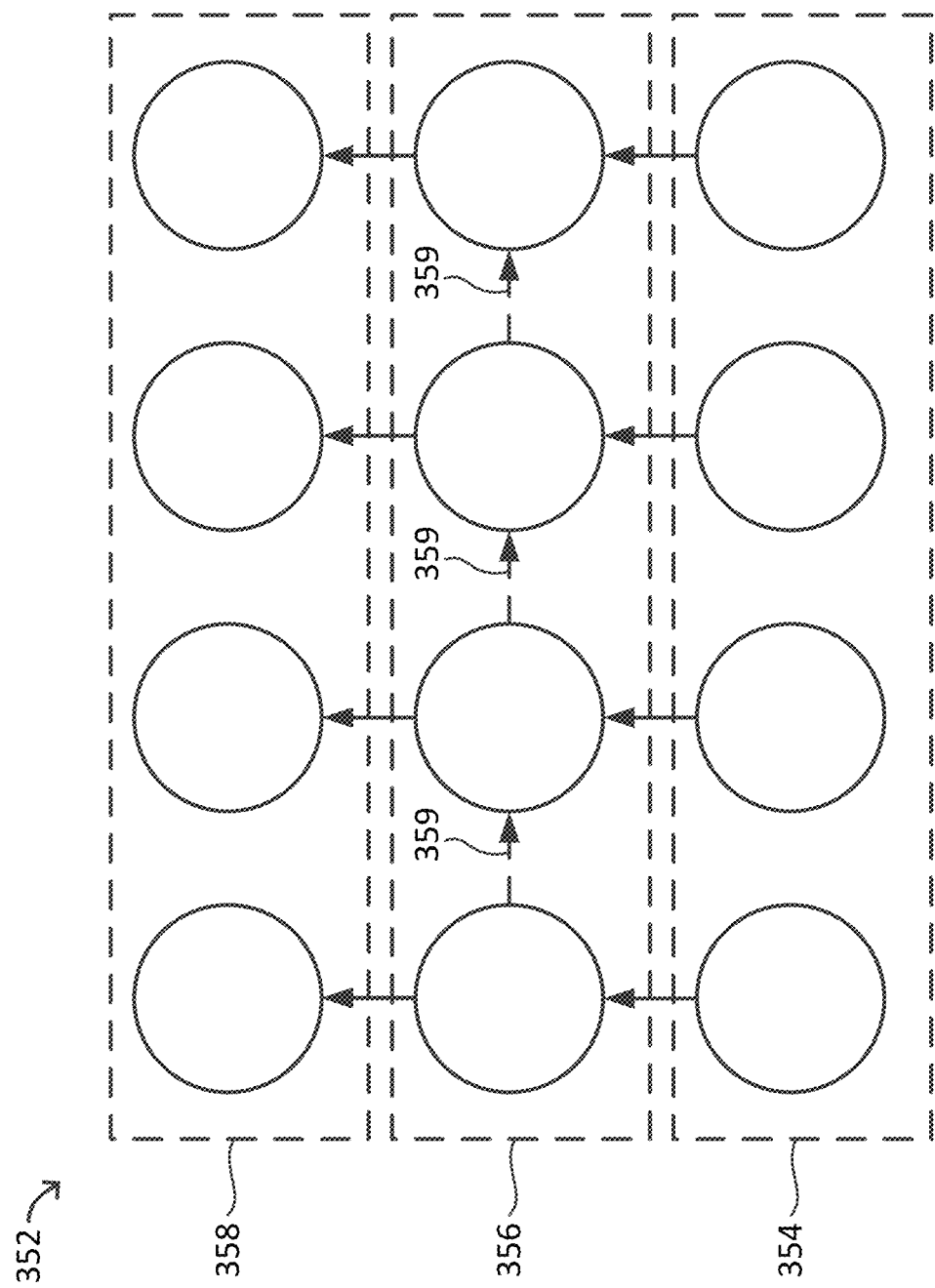
FIG. 10 is a diagram illustrating module of a feature extraction module of an embodiment.

As illustrated in FIG. 10, the RNN module 352 comprises an input 354, a hidden layer 356 that receives the input 354, and an output 358 of the hidden layer 356. The input 354 of the RNN module 352 may be the output 350 of the ResNet Module 344. The output 358 of the hidden layer 356 may be the temporal features 370 output by the RNN module 352, referenced in FIG. 3. As illustrated by the dashed arrows 359 in FIG. 10, which indicate an edge to a next time step, the output 358 of the hidden layer depends on a current one of the input 354 and a previous state of, for example, the hidden layer 356. For example, the previous state of the hidden layer 356 may be an output of the hidden layer 356 based on a previous input 354.

Referring to FIG. 3, the temporal features 370 output by the RNN module 352 of the feature extraction module 340 may be input into the signal classification module 380 which may be trained and may determine whether the ECG signals 310 correspond to a normal, AFib, or VFib signal. The signal classification module 380 may output a result 390 that identifies whether the ECG signals 310 corresponds to a normal, AFib, or VFib signal. Accordingly, the framework 300 is able to identify a type of the ECG signals. The result 390 may be input into a display for display, or a displaying system, comprising at least one processor and memory, for display on a display.

At least one processor may be configured as the image generation module 320, the feature extraction module 340, and the signal classification module 380 such that the at least one processor performs the functions of the modules. For example, a processor or processors of the at least one processor may together perform the functions of one or more of the modules, or a respective processor or processors of the at least one processor may perform the functions of each module.

Figure 11:
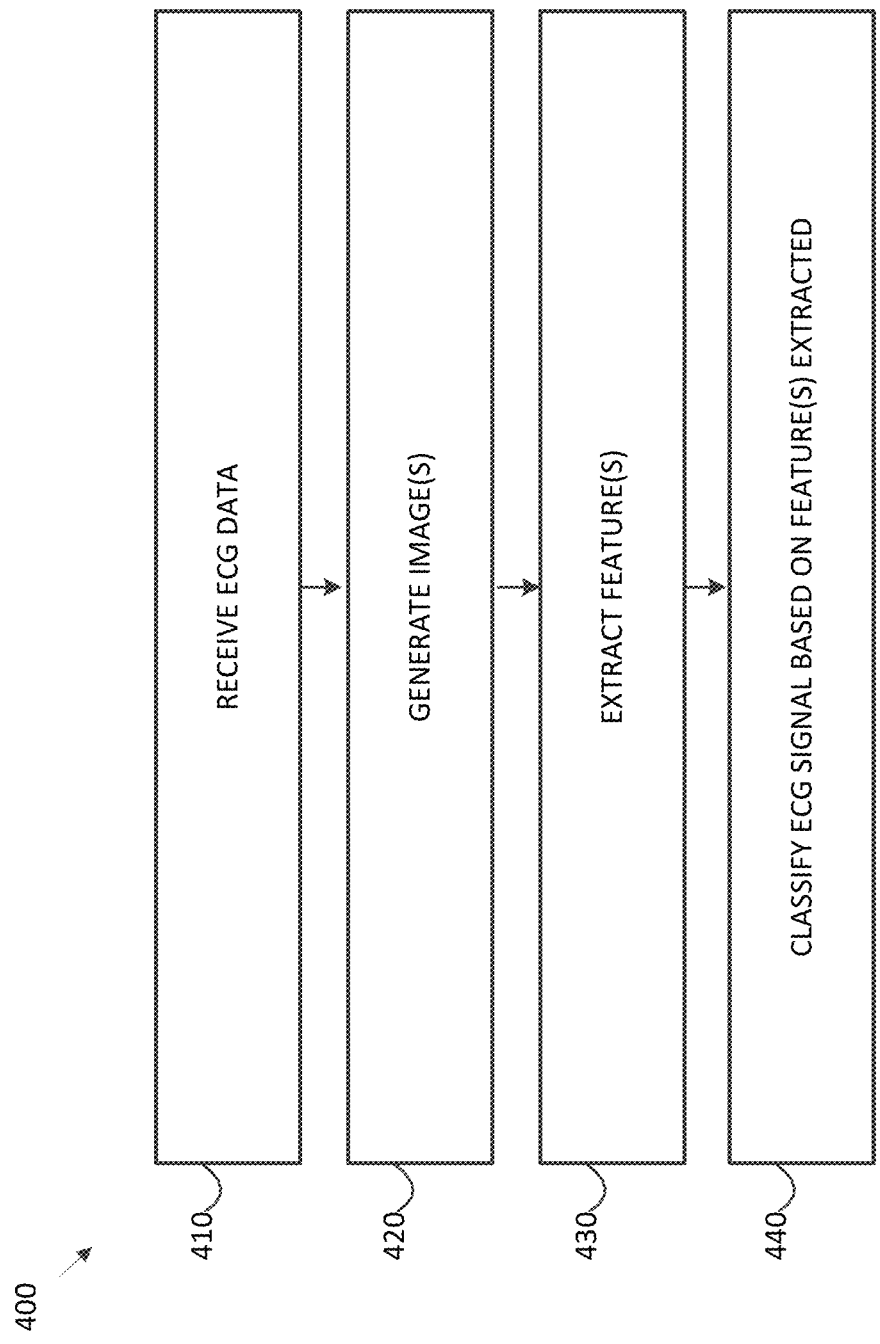
FIG. 11 is a flowchart of a method of performing ECG analysis, according to embodiments.

FIG. 11 illustrates a method 400 performed by the at least one processor of an embodiment of the present disclosure.

In the embodiment, the at least one processor may receive multiple ECG signals 310 (410). Following, the at least one processor may generate, based on the ECG signals 310, images such as the image sequence 330 by performing the functions of the image generation module 320 (420). Afterwards, the at least one processor may extract temporal features 370 from the images by performing the functions of the feature extraction module 340, including the functions of the feature map extraction module 341, the ResNet module 344, and the RNN module 352 (430). Then, the at least one processor may classify an ECG signal and produce a result 390 by performing the functions of the signal classification module 380 (440).

Figure 12:
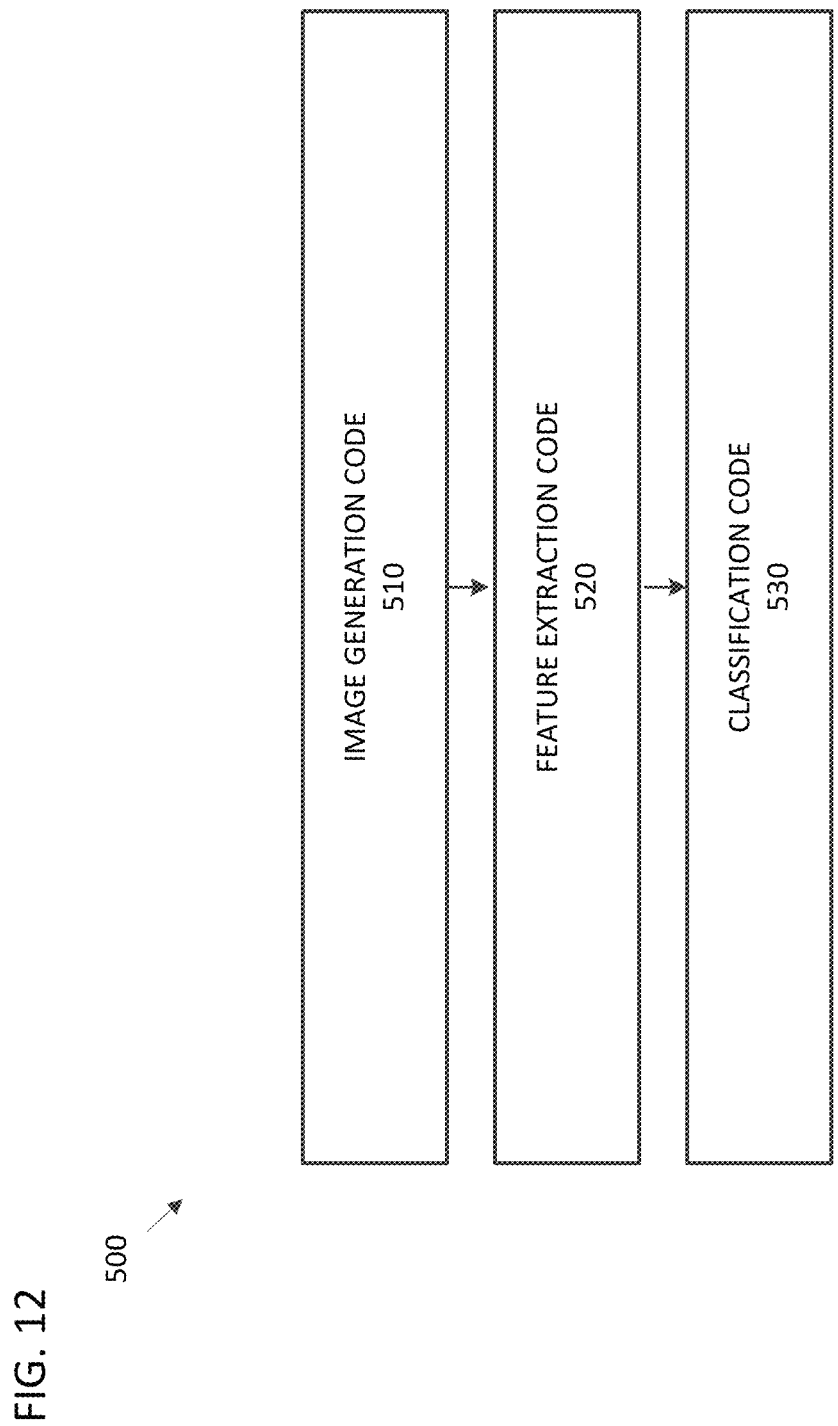
FIG. 12 is a diagram of an apparatus for performing an ECG analysis, according to embodiments.

FIG. 12 is a diagram of an apparatus 500 for performing ECG analysis, according to embodiments. As shown in FIG. 12, the apparatus 500 includes image generation code 510, feature extraction code 520, and classification code 530. The apparatus 500 may include at least one memory that stores one more of the codes, and at least one processor to perform one or more of the codes.

The image generation code 510 may be configured to cause at least one processor to perform the functions of the image generation module 320. The feature generation code 520 may be configured to cause at least one processor to perform the functions of the feature extraction module 340, including the functions of the feature map extraction module 341, the ResNet module 344, and the RNN module 352. The classification code 530 may be configured to cause at least one processor to perform the functions of the signal classification module 380.

Embodiments of the present disclosure provide an end-to-end framework. Compared to existing approaches, embodiments of the present disclosure may take the difference between leads into account, and can handle multi-lead ECG signals. Embodiments of the present disclosure generate image sequences as an input of a module of a framework, which contain spatial and temporal information. Additionally, embodiments of the present disclosure may be deep learning based, robust to noise and differences in data, and time efficient in comparison to manual work and conventional methods.

In an embodiment, different types of images can be used or combined for the image generation stage. In an embodiment, with respect to the deep learning model, the number of ResNet blocks 345 can be adjusted based on the data. In an embodiment, the framework 300 can be extended to other applications to detect different type of arrhythmia.

Even though particular combinations of features are recited in the claims and/or disclosed in the specification, these combinations are not intended to limit the disclosure of possible implementations. In fact, many of these features may be combined in ways not specifically recited in the claims and/or described in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method of performing electrocardiography ("ECG") analysis by at least one processor, the method comprising:
    receiving ECG data that is from a plurality of leads;
    generating an image based on the ECG data, wherein the image generated based on the ECG data is a first plot including three dimensions of information concerning a plurality of ECG signals, from the plurality of leads;
    obtaining a feature map, from the image that is the first plot;
    inputting the feature map to a first neural network, the first neural network configured to generate an output based on the feature map inputted;
    inputting the output of the first neural network to a second neural network, the second neural network configured to obtain at least one temporal feature of the first plot based on the output of the first neural network and a previous state of the second neural network; and
    classifying a signal included in the ECG data based on the at least one temporal feature obtained by the second neural network,
    wherein the generating the image that is the first plot comprises:
        generating a plurality of second plots by generating, for each of the plurality of leads, a respective second plot including two dimensions of information concerning a respective ECG signal from a respective one of the plurality of leads, and
        forming the first plot, that is the image from which the feature map is obtained, by stacking the plurality of second plots.

2. The method of claim 1, wherein the generating the plurality of second plots comprises:
   detecting a first peak and a second peak of one ECG signal of the plurality ECG signals corresponding to one of the plurality of leads;
   extracting a first part of the ECG signal starting at the first peak;
   extracting a second part of the ECG signal starting at the second peak;
   combining the first part and the second part of the ECG signal to form one of the plurality of second plots.

3. The method of claim 1, wherein the image generated based on the ECG data is a waterfall plot that includes the three dimensions of information concerning the plurality of ECG signals from the plurality of leads.

4. The method of claim 1, wherein the first neural network is a residual neural network ("ResNet").

5. The method of claim 4, wherein the ResNet is a model including a plurality of ResNet blocks provided in series, each of the ResNet blocks being a convolution neural network.

6. The method of claim 5, wherein each of the ResNet blocks includes at least one weight layer to which an input of the ResNet block is applied, at least one rectified linear unit ("ReLU"), and an addition layer configured to add together the input of the at least one weight layer of the ResNet block with an output of the at least one weight layer of the ResNet block.

7. The method of claim 1, wherein the second neural network is a recurrent neural network ("RNN").

8. The method of claim 1, wherein the classifying the signal comprises determining whether the signal corresponds to a normal signal, an atrial fibrillation ("AFib") signal, or a ventricular fibrillation ("VFib") signal.

9. The method of claim 8, further comprising:
   outputting a result of the determining whether the signal corresponds to the normal signal, the AFib signal, or the VFib signal to a display to display the result.

10. The method of claim 1, wherein
    the first neural network is a residual neural network ("ResNet"), and
    the second neural network is a recurrent neural network ("RNN").

11. A device for performing electrocardiography ("ECG") analysis, the device comprising:
    at least one memory configured to store computer program code; and
    at least one processor configured to access the computer program code and operate as instructed by the computer program code, the computer program code including:
    image generation code configured to cause the at least one processor to generate an image based on ECG data received by the device from a plurality of leads, wherein the image generated based on the ECG data is a first plot including three dimensions of information concerning a plurality of ECG signals, from the plurality of leads;
    feature extraction code configured to cause the at least one processor to:
      obtain a feature map from the image that is the first plot,
      input the feature map to a first neural network, the first neural network configured to generate an output based on the feature map inputted,
      input the output of the first neural network to a second neural network, the second neural network configured to obtain at least one temporal feature of the first plot based on the output of the first neural network and a previous state of the second neural network, and
    classification code configured to cause the at least one processor to classify a signal included in the ECG data based on the at least one temporal feature obtained by the second neural network,
    wherein the image generation code is configured to cause the at least one processor to generate the first plot by:
      generating a plurality of second plots by generating, for each of the plurality of leads, a respective second plot including two dimensions of information concerning a respective ECG signal from a respective one of the plurality of leads, and
      forming the first plot, that is the image from which the feature map is obtained, by stacking the plurality of second plots.

12. The method of claim 11, wherein
    the first neural network is a residual neural network ("ResNet"), and
    the second neural network is a recurrent neural network ("RNN").

13. The device of claim 11, wherein the first neural network is a residual neural network ("ResNet").

14. The device of claim 13, wherein the ResNet is a model including a plurality of ResNet blocks provided in series, each of the ResNet blocks being a convolution neural network.

15. The device of claim 14, wherein each of the ResNet blocks includes at least one weight layers to which an input of the ResNet block is applied, at least one rectified linear unit ("ReLU"), and an addition layer configured to add together the input of the at least one weight layer of the ResNet block with an output of the at least one weight layer of the ResNet block.

16. The device of claim 11, wherein the classification code is configured to cause the at least one processor to classify the signal by determining whether the signal corresponds to a normal signal, an atrial fibrillation ("AFib") signal, or a ventricular fibrillation ("VFib") signal.

17. The device of claim 16, further comprising:
    outputting a result of the determining whether the signal corresponds to the normal signal, the AFib signal, or the VFib signal to a display to display the result.

18. A non-transitory computer-readable medium storing instructions, the instructions comprising: one or more instructions that, when executed by at least one processor for performing electrocardiography (ECG) analysis, cause the at least one processor to:
    receive ECG data that is from a plurality of leads;
    generate an image based on the ECG data, wherein the image generated based on the ECG data is a first plot including three dimensions of information concerning a plurality of ECG signals, from the plurality of leads;
    obtain a feature map from the image that is the first plot;
    input the feature map to a first neural network, the first neural network configured to generate an output based on the feature map inputted;
    input the output of the first neural network to a second neural network, the second neural network configured to obtain at least one temporal feature of the first plot based on the output of the first neural network and a previous state of the second neural network; and
    classify a signal included in the ECG data based on the at least one temporal feature obtained by the second neural network, wherein the one or more instructions are configured to cause the at least one processor to generate the first plot by:
generating a plurality of second plots by generating, for each of the plurality of leads, a respective second plot including two dimensions of information concerning a respective ECG signal from a respective one of the plurality of leads, and
forming the first plot, that is the image from which the feature map is obtained, by stacking the plurality of second plots.

\* \* \* \* \*